(12) United States Patent
Morgan

(10) Patent No.: US 8,166,975 B2
(45) Date of Patent: May 1, 2012

(54) COMBINATION PROPHYLACTIC PACKAGE AND DISPENSER

(76) Inventor: Marcus Morgan, Toluca Lake, CA (US)

( * ) Notice: Subject to any disclaimer, the term of this patent is extended or adjusted under 35 U.S.C. 154(b) by 363 days.

(21) Appl. No.: 12/419,040

(22) Filed: Apr. 6, 2009

(65) Prior Publication Data

US 2010/0252051 A1    Oct. 7, 2010

(51) Int. Cl.
*A61F 6/04* (2006.01)
*A61F 5/44* (2006.01)
*B65D 85/08* (2006.01)

(52) U.S. Cl. .................... 128/844; 206/69; 604/352
(58) Field of Classification Search .......... 128/842, 128/844, 918, 830; 206/69, 364; 604/352, 604/351, 349, 347, 346, 327, 317
See application file for complete search history.

(56) References Cited

U.S. PATENT DOCUMENTS

| | | | |
|---|---|---|---|
| 5,170,887 A | 12/1992 | Potts et al. | |
| 5,351,698 A | 10/1994 | Wheeler et al. | |
| 5,437,286 A * | 8/1995 | Stratton | 128/844 |
| 5,549,120 A | 8/1996 | Persson et al. | |
| 5,549,196 A * | 8/1996 | Kassman | 206/69 |
| 5,605,164 A | 2/1997 | Wilson, III | |
| 5,651,374 A | 7/1997 | Wester | |
| 5,758,659 A | 6/1998 | Thompson | |
| 6,089,231 A | 7/2000 | Thompson | |
| 6,095,145 A | 8/2000 | Sadlo | |
| 6,718,983 B1 | 4/2004 | Suzuki | |
| 6,913,018 B2 * | 7/2005 | Van Rensburg | 128/844 |
| 6,929,118 B1 * | 8/2005 | Izz | 206/69 |

OTHER PUBLICATIONS

Webpage, Pronto Condoms, The best way to get it on!, www.prontocondoms.co.za/index.htm, 2 pgs., Dec. 18, 2008.
Webpage, Pronto Condoms, The best way to get it on!, www.prontocondoms.co.za/demo.htm, 1 pg., Dec. 18, 2008.
Webpage, Let's Get in on—Condom Applicator Wins Design Prize: TreeHugger, www.treehugger.com/files/2007/04/pronto-condoms.php, Leonora Oppenheim London, UK on Apr. 1, 2007, 1 pg., Apr. 6, 2009.

* cited by examiner

*Primary Examiner* — Patricia Bianco
*Assistant Examiner* — Tarla Patel
(74) *Attorney, Agent, or Firm* — Fulwider Patton LLP

(57) ABSTRACT

A package housing a condom and dispenser for holding the peripheral wall of the condom folded into a tubular accordion stack and operable upon application of a predetermined force to the closed end of the condom to meter the folds in progression.

1 Claim, 5 Drawing Sheets

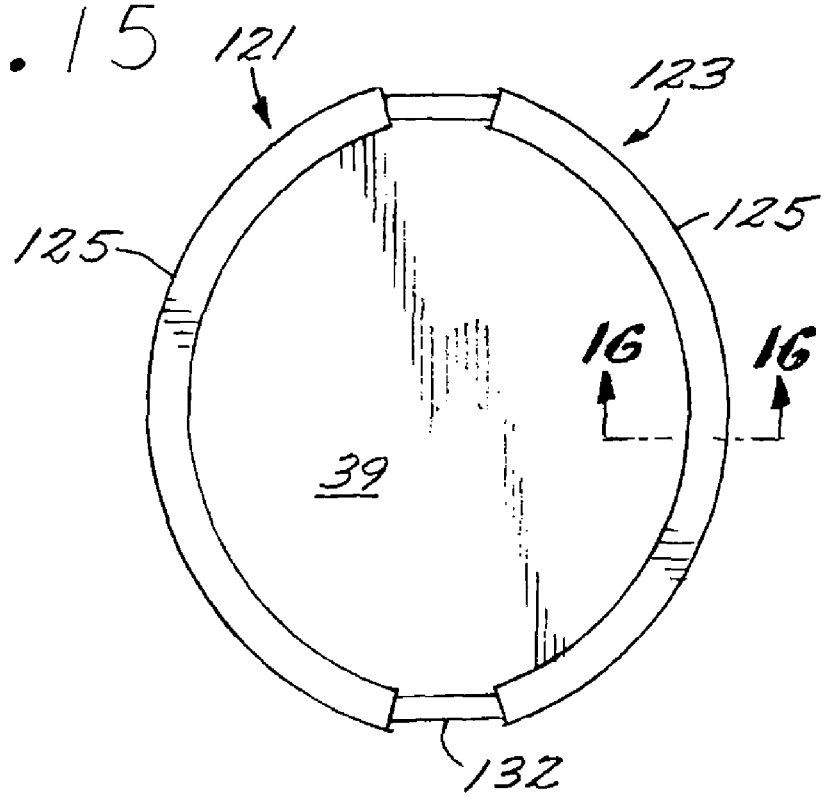
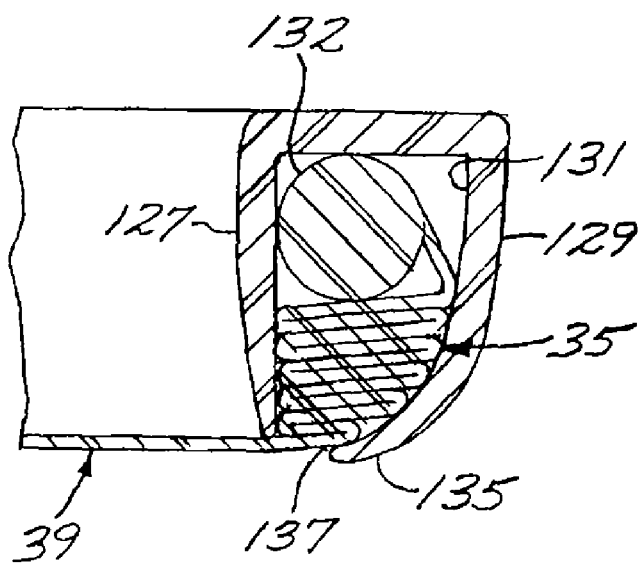

COMBINATION PROPHYLACTIC PACKAGE AND DISPENSER

BACKGROUND

1. Field of the Invention

The present invention relates to condoms and packaging for therefore

2. Description of the Prior Art

Amongst the many purposes served by condoms is limitations on the transmission of diseases. In recent years there has been a significant increase in the incidence and spread of sexually transmitted diseases which has driven the public to utilize condoms as a prophylactic measure to reduce the risk of infection and transmission. The advantage of avoiding contact to the condom by a partner with an unknown sexual history are apparent.

One of the causes for the increase in incidents and rate of transmission of sexually transmitted diseases are the development of increasingly antibiotic-resistant strains of disease-causing organisms such as those responsible for syphilis and gonorrhea. Another factor has been the absence of any effective cure for the acquired immunodeficiency.

Factors bearing on the partner's election to make use of condoms is the delay necessary for donning of the condom and the fact that an improperly applied condom will detract from the comfort of the users. Many efforts have been made to provide condoms that do not counter the prevailing mood and which are easily positionable as by the utilization of a split ring holder. It has been proposed to provide an annular C-shaped condom holder for receipt of a rolled or folded condom. A device of this type is shown in U.S. Pat. No. 4,738,357 to Martin et al. Other efforts have lead to a proposal that condoms be housed in a U-shaped package in a rolled or folded configuration as shown in U.S. Pat. No. 5,437,286 to Stratton. Deficiency in devices of this type is that the rolls or folds may be dispensed in a relatively disorganized manner which may result in wrinkles along the length of the condom or incomplete application which may detract from the comfort and pleasure of the partner as well as the prophylactic effectiveness.

Other efforts to improve the construction of condoms to facilitate the rapid and convenient donning has lead to the proposal that the packaging be split so it may be separated and the parts of the package drawn laterally apart to stretch the open end of the condom. It has been proposed to provide condom packaging which includes an annular ridge or hook attachment means for holding the end of the hand ring of the condom while the condom is being donned. A device of this type is shown in U.S. Pat. No. 5,170,887 to Potts et al. Other condom devices include split packaging facilitate spreading of the open end of the condom. See U.S. Pat. No. 5,549,120 to Persson et al. and U.S. Pat. No. 6,913,018 to Van Rensburg. Thus, prior to the present invention, users have been faced with the dilemma of utilizing condoms which provide certain challenges to donning thereof and which risk incomplete or improper application, thus detracting from the enjoyment of the partners.

SUMMARY OF THE INVENTION

The present invention includes a package and condom apparatus including a dispenser for releasably holding the peripheral wall of the condom in a pack of organized accordion folds.

BRIEF DESCRIPTION OF THE DRAWINGS

FIG. 15 is a top plan view of a fourth embodiment of the apparatus of the present invention; and FIG. 16 is a transverse sectional view, in enlarged scale, taken along line 16-16 of FIG. 15.

DETAILED DESCRIPTION OF THE PREFERRED EMBODIMENTS

Figure 1:
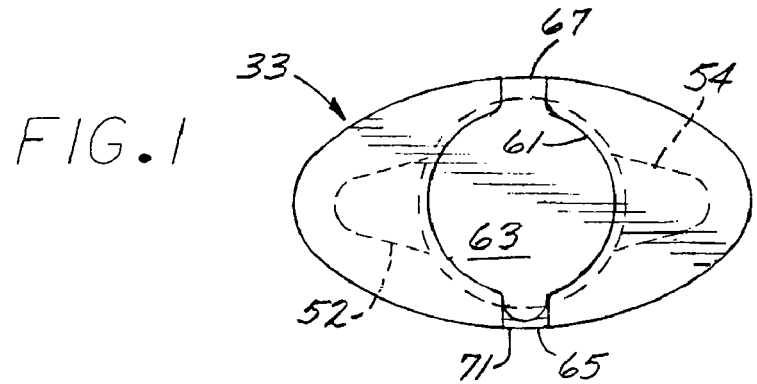
FIG. 1 is a top plan view of a combination package and condom apparatus of the present invention.
Figure 2:
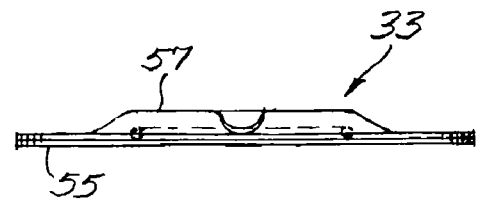
FIG. 2 is a front view of the apparatus shown in FIG. 1.
Figure 3:
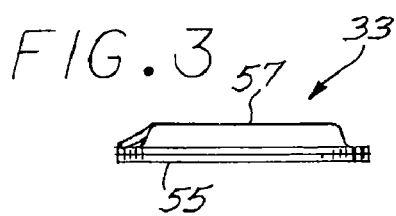
FIG. 3 is an end view of the apparatus shown in FIG. 1.
Figure 5:
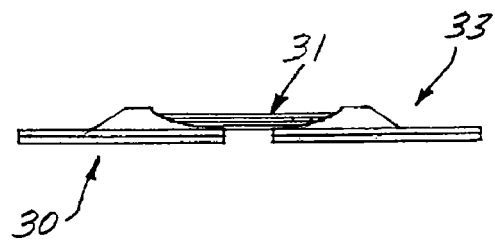
FIG. 5 is a front view of the apparatus shown in FIG. 4.
Figure 6:
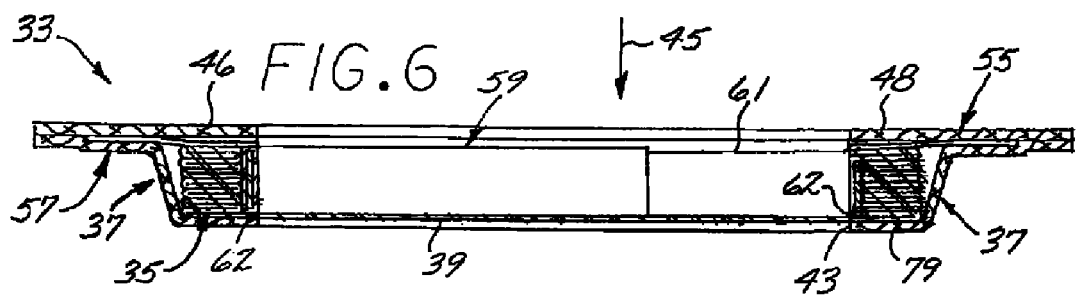
FIG. 6 is a transverse sectional view, in enlarged scale, taken along the line 6-6 of FIG. 4 and inverted.

Referring to FIGS. 1, 5 and 6, the combination condom and packaging apparatus 30 of the present invention includes, generally, a condom 31 packaged in a package 33 to hold a series of accordion folds defining a stack 35 held releasably in place by a dispenser 37. The package 33 is openable to form apertures 41 and 43 on the respective back and front sides thereof for axial displacement of the closed end of the condom in the direction of the directional arrow 45 to provide progressive dispensing of the folds from the end of the stack proximate the closed end of the condom.

Condoms are typically constructed of thin walled, highly flexible thermoplastic polyethylene material to form a cylindrical shape having a closed end 39 an open end 51. In one preferred embodiment the condom is formed at the opposite sides of its open end with diametrically outwardly flared ears 52 and 54.

As is well-known in the art, condoms may be constructed by blow-extrusion forming to provide a tubular film or may be formed in a film over a male mold. For the purposes of this invention, the sheath forming the condom may be formed by any well-known specific structure or molding. Materials particularly useful for forming the condom articles of this invention include elastomeric materials, as well as flexible non-elastomeric materials such as nylons, polyethylene terephthalate, and olefinic homopolymers and co-polymers; e.g., ultra low density polyethylene.

The combination condom package depicted will typically be housed an external package or envelope which is openable to expose the subject internal package 33. For the purposes of illustration, the package 33 is depicted constructed of conventional packaging material and formed with elliptical back and front walls 55 and 57, respectively.

Figure 4:
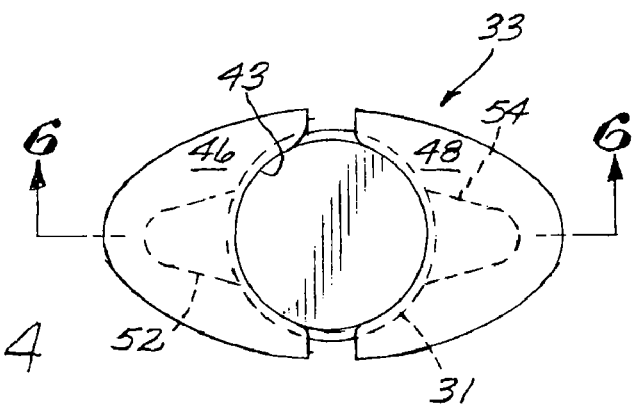
FIG. 4 is a top plan view similar to FIG. 1 but showing a seal separated from the package.

The front wall 57 is sealed parametrically to the back wall 55 and, as manufactured, the walls are formed with weakened transverse, spaced apart lines 61 which may define circular discs 63 on the back and front walls, 55 and 57, respectively and joined around the front and back sides by narrow straps 65 and 67 to cooperate in forming a releasable seal. In the preferred embodiment, the seal is formed with a pull tab 71 which may be pulled to remove the discs and straps 65 and 67 along the weakened lines to leave the package formed with the apertures 41 and 43 in the back and front walls, respectively, as depicted in FIGS. 4, 5 and 6 while also separating the package into opposite halves 46 and 48.

Figure 8:
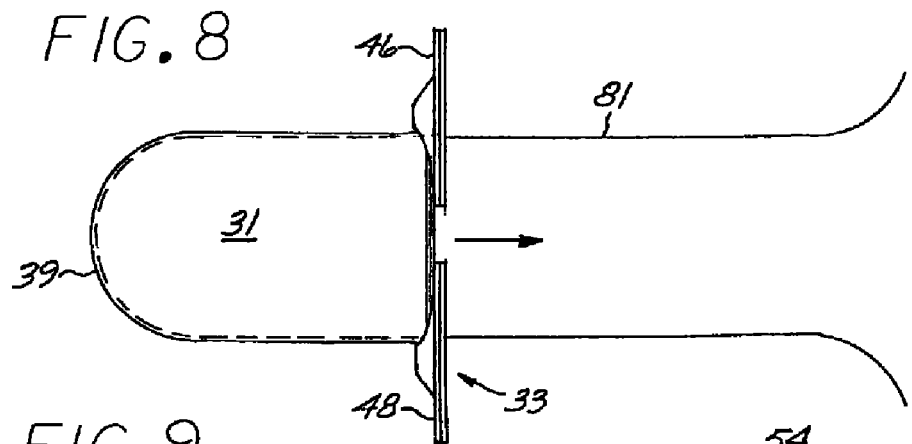
Figure 9:
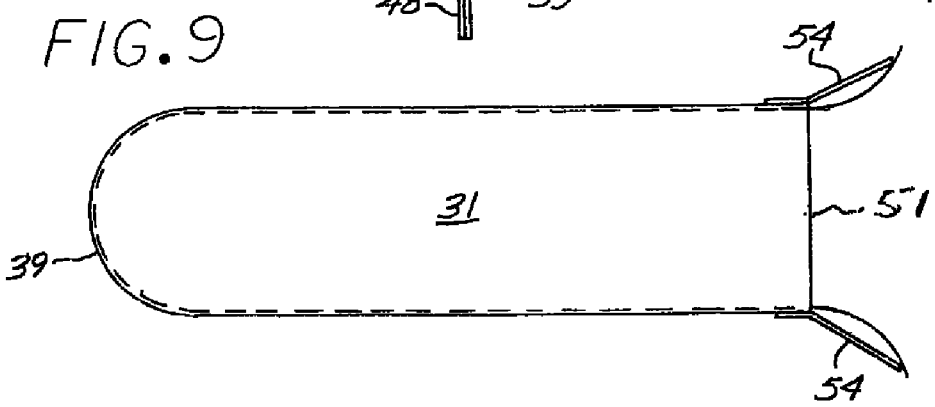
Figure 10:
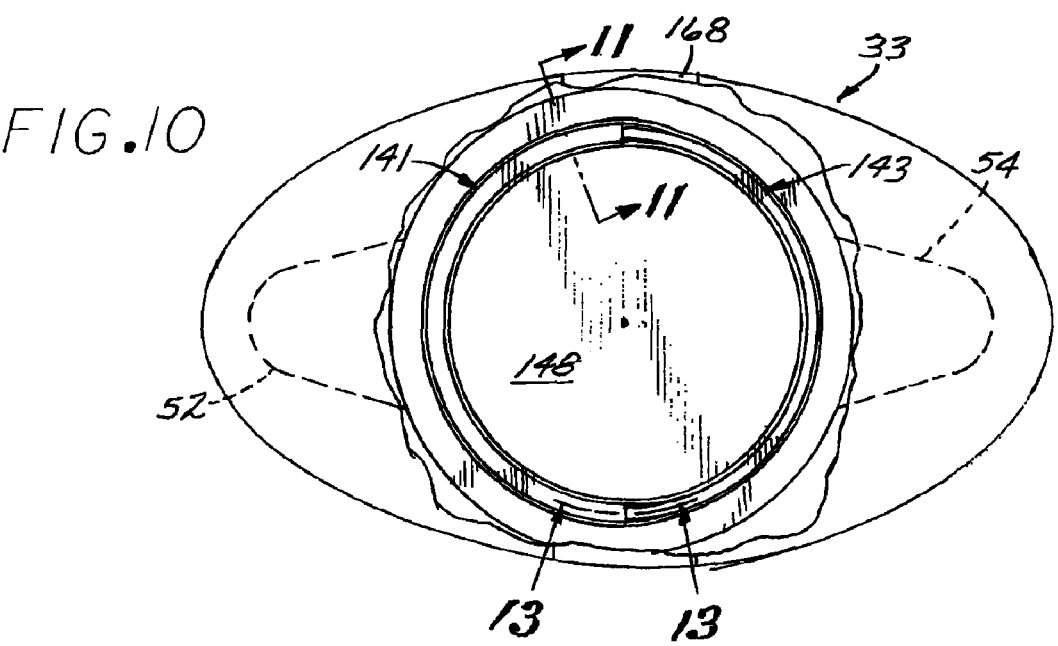
FIG. 10 is a top plan view of a second embodiment of the package and condom apparatus of the present invention, partially broken away.

The walls 55 and 57 provide sufficient body to hold the folds of the stack 35 organized under the bias of the upwardly acting force on the rim 79 of the side wall 37 to thus maintain the folds slightly compressed in their stacked relationship until such time as a penis 81 is entered through the aperture 41 and pressed against the closed end 39 with sufficient force to commence dispensing of the folds. The folds will typically be drawn distally unfolding from the stack in progression from the location proximate the closed end 39 to thus allow the penis 81 to be progressively sheathed by the deployed condom as depicted in FIGS. 8 and 9.

It will be appreciated in some embodiments that the wall 55 is constructed of foil with sufficient resiliency to cause the rim 79 to be biased upwardly as viewed in FIG. 6 to thus maintain a bias on the stack 35 as the folds are dispensed in an orderly fashion.

Disposed on the radially interior sides of the diametrically opposite sides of the stack 35 are semi-circular ring-like female and male distenders 59 and 60 to cooperate at their respective distal edges with the respective rims 79 to define respective narrow slots 62. The ears 52 and 54 flare generally diametrically outwardly from the respective distenders 59 and 60. The opposite ends of the male distender 60 telescope into the respective open ends of the male distender 59 to be drawn therefrom as the package halves 46 and 48 are drawn apart.

As will be appreciated, that in use, once the seal straps 65 and 67 are removed, the opposite sides of the package are separated laterally so that the user might grasp those sides individually squeezing down on the ears 52 and 54 sandwiched between the front and back walls 55 and 57 to spread the package sides diametrically apart to thus facilitate the opening of the open end of the condom.

It will be appreciated that the user will access the exterior envelope in which the package 33 is contained The opening tab 71 may than be grasped and peeled back to separate the back wall disk 63, straps 65 and 67 and corresponding front disk 63 to thus separate the package halves 46 and 48 and open the respective apertures 41 and 43 (FIG. 6). The user may then grasp the opposite halves of the package and draw those halves apart causing the ears 52 and 54 to draw the respective distenders diametrically outwardly to stretch the condom to open condition.

Figure 7:
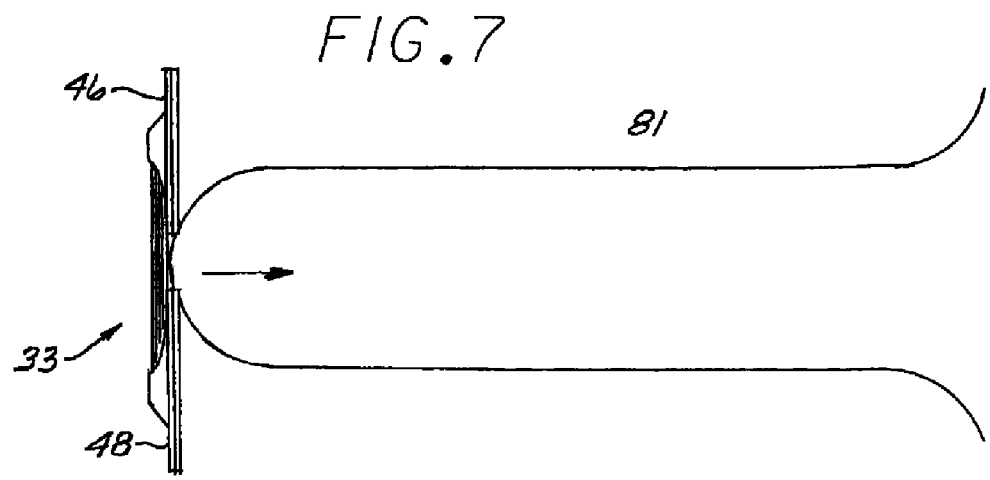
FIGS. 7, 8 and 9 are diagrammatic front views of the apparatus shown in FIG. 1 being applied to a penis.

Then, as the package 33 is drawn over the penis 81, as shown in FIG. 7, a sufficient force will be applied to the closed end 39 to drive that end distally and draw the condom wall out the slots 62 to unfold the folds of the stack 35 progressively from the dispenser against the modest retaining pressure afforded by the rim 79 against the distal edges of the distenders 59 and 60 acting as a pusher wall to push radially outwardly toward the respective rims 79 to progressively sheath the penis in a smooth and rapid manner. Once donning of the condom has been completed, the opposite halves of the package 33 may be discarded.

Referring back to FIGS. 10-13, in one embodiment of the present invention, a pair of semi-circular female and male holders defining distenders, generally designated 141 and 143, are formed integral with a condom, generally designated 144, and are telescoped together at their confronting ends and lay at the radial interior of the diametrical opposite sides of the stack 35. The female distender 141 is generally channel shaped to define a tube to terminate in respective open female ends 151 and 153 for slidable receipt of the male ends of the distender 143. The distenders 141 and 143, while being resilient, have sufficient body and memory to generally cooperate and maintain a generally circular in-plan-view configuration for stacks.

Figure 11:
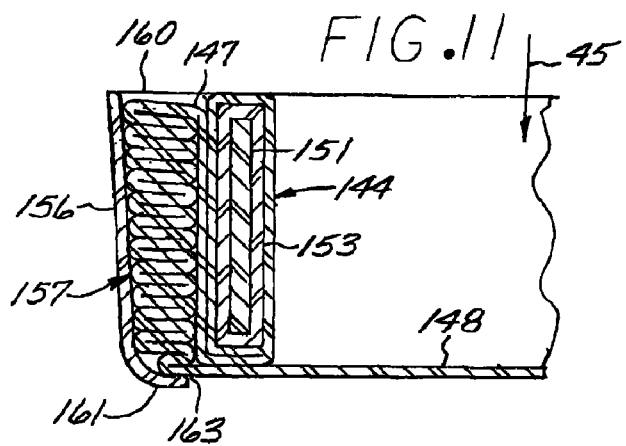
FIG. 11 is a transverse sectional view, in enlarged scale, taken along line 11-11 of FIG. 10.
Figure 12:
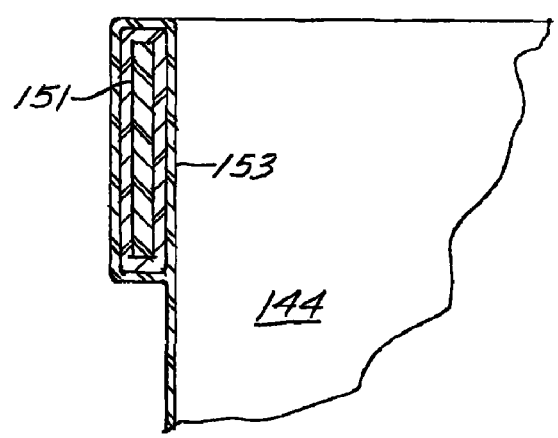
FIG. 12 is a partial transverse sectional view, in enlarged scale, similar to FIG. 11 but with the fold stack unfolded and the package received.
Figure 13:
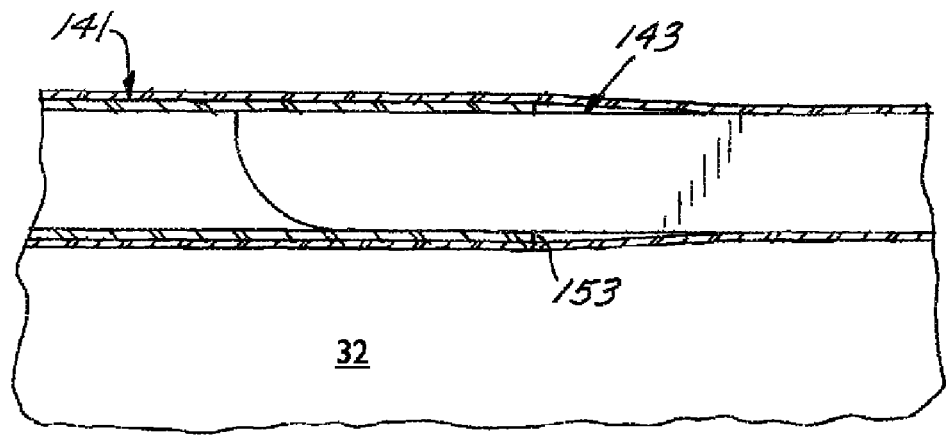
FIG. 13 is a partial transverse sectional view, in enlarged scale, taken along line 13-13 of FIG. 10.

For these embodiments, a package, generally designated 146, envelopes the condom and in some embodiments is constructed to be opened to expose apertures on the front and back sides for access by the penis in the direction of the directional arrow 45 to push the end wall 148 distally and withdraw the folds. Referring to FIGS. 11 and 12, the distenders may be constructed to lay along the radially inner sides of the diametrical opposite sides of the stack 35 or may be partially incorporated in the open extremity of the condom.

As shown, the wall of the condom on one diametrical half may feed off the stack 35 at 147 to lay axially along the radially interior side thereof and turn radially inwardly to then turn axially upwardly as viewed in FIG. 11 and to the turn outwardly and back down to cooperate in forming a generally rectangular-in-longitudinal cross section stack. The open end of the condom is formed in one diametrical with rectangular in cross section hollow tube 153 open at its circumferential end 155 to telescopically receive a tab 161 defining one circumferential end of the male distender 143. The radially outer walls 156 of the package cooperate with the respective distenders 141 and 143 to form an annular dispenser cavity 157. The proximate and distal extremities of the radial walls 155 turn radially to define, respectively, a retainer flange 160 and retainer fringes 161 to cooperate in releasably holding the respective stacks.

In operation, it will be appreciated that the seal may be opened to expose front and back apertures and the penis may be entered in the direction of the directional arrow 45 to press the wall 148 distally as the ears 52 and 54 are drawn diametrically outwardly to draw the distenders 141 and 143 to fully open the mouth of the condom. As will be appreciated the package may be separable at 168 so the ears 52 and 54 can be drawn diametrically outwardly. The peripheral wall of the condom will thus be drawn progressively distally outwardly from the annular dispenser cavity 157 to meter folds out through the respective stacks 163.

Figure 14:
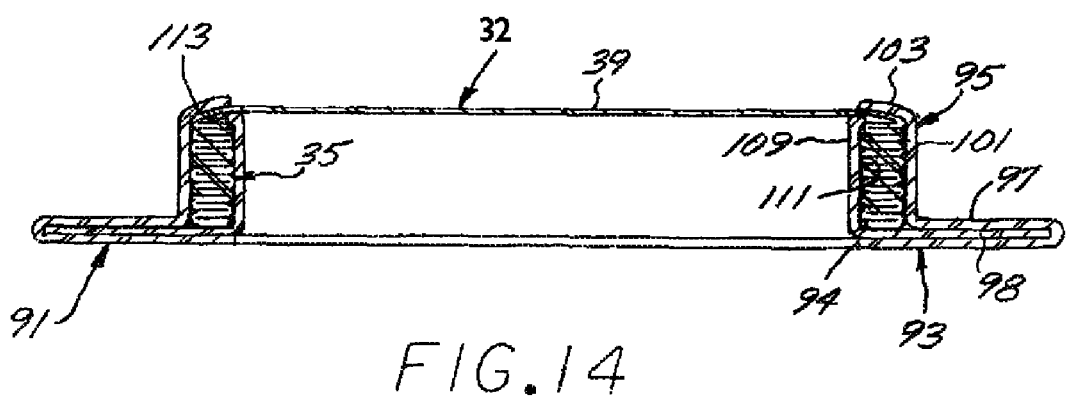
FIG. 14 is a transverse sectional view of a third embodiment of the combination of condom and packaging apparatus of the present invention.

Referring to FIG. 14, in a further embodiment of the present invention, a package, generally designated 91, includes a back wall 93 openable to form an aperture 94. On the back wall is a mounted resilient channel section, generally designated 95, which includes a planar mounting tab 97 turned upwardly on its radially inner extremity to form a semi cylindrically shaped channel section 101 formed at its distal extremity with an inwardly resilient turned retainer lip 103. The section of the back walls are turned back on themselves to sandwich therebetween respective tabs 98 which project radially inwardly and turn axially distally to form a cooperating channel section 109 which cooperates with the channel section 101 to form a semicircularly shaped dispenser channel 111 cooperating to releasably retain the fold stack 35 formed by the peripheral wall of the condom. The channel section 109 extends proximally and turns radially outwardly to form an annular resilient retainer flange 113 cooperating with the lip 103 to form an annular slot opening having a radial width slightly greater than the thickness of the condom wall to thereby cooperate in forming a dispenser to progressively dispense the folds of the stack 35.

Thus, in this embodiment, when the penis encounters the closed end 39 of the condom with sufficient force to slightly flex the retainer flange 113 and continues progression, the folds of the stack 35 will be drawn progressively from the stack to thus sheath the penis in a smooth and progressive manner.

The embodiment of the present invention shown in FIGS. 15 and 16, includes, a pair of semicircular-in-plan view combination distenders and dispensers, generally designated 121 and 123.

As shown in FIG. 16, the combination distenders and dispensers 121 and 123 include respective distally opening dispenser channels 125 formed with respective concentric, annular flanges 127 and 129 cooperating to form a respective semicircular storage compartments 131 for receipt of the condom bead 132 and condom folds in a stack 35. The interior flange 127 is generally cylindrically shaped. The exterior flange 129 projects distally and turns radially inwardly to form a resilient retainer finger 135 cooperating with the distal tip of the flange 127 to form an annular slot 137 for progressively and controllably dispensing the folds of the stack 35 as the penis moves distally relative thereto. The channel 131 is thus reduced in radial cross section in the distal direction to house the folds of the search progressively diminishing in radial width in the distal direction.

From the foregoing, it will be appreciated that the combination packaging and condom of the present invention provides an economical and practical means for housing and dispensing of the condom in an orderly and rapid fashion for convenience of donning and assurance of proper sheathing.

I claim:

1. A combination condom and package apparatus comprising:
 a condom device having a cylindrical peripheral wall a defining back entry end and a front closed end wall and configured on one diametrical side of the entry end with a distender including one diametrical side ring shaped female distender formed with open ends, the condom configured in the entry end, opposite the one diametrical side with a ring shaped male distender having opposite ends received slidably in the respective open ends and further configured with ears projecting diametrically outwardly from the respective male and female distenders, the peripheral wall being formed with folds stacked on one another to form a cylindrical stack having back and front ends and disposed radially outside of the distender;
 a cylindrically shaped package device including flexible oval front and back walls disposed on the respective front end and closed end of the condom device, the front and back walls being separable to cooperate in forming diametrically oppositely disposed package halves receiving the respective ears, and to from there between respective centrally disposed back and front apertures, the front walls of the halves further including respective rims disposed against the front end of the stack, and cooperating with the respective male and female distenders to form respective slots configured for the peripheral wall to pass therethrough, and further operative to, when the closed end wall of the condom is pushed out through the front aperture, meter the folds of the stack progressively outwardly through the slot whereby a user may grasp the opposite package halves to compress the respective front and back walls against the opposite sides of the respective ears, and draw the package halves laterally apart to draw the ears apart, thereby drawing the male and female distenders laterally apart so that, upon a penis being inserted through the back aperture and engaged against the closed end wall and the closed end wall pushed distally through the front aperture the folds will be drawn progressively from the respective slots.

\* \* \* \* \*